United States Patent [19]

Gessman

[11] 4,340,065
[45] Jul. 20, 1982

[54] METHOD AND APPARATUS FOR DISPLAYING ELECTROCARDIOGRAM SIGNALS

[76] Inventor: Lawrence J. Gessman, 100 Haven Ave., Apartment 6D, New York, N.Y. 10032

[21] Appl. No.: 74,475

[22] Filed: Sep. 11, 1979

[51] Int. Cl.³ .............................................. A61B 5/04
[52] U.S. Cl. .................................................... 128/712
[58] Field of Search ................................. 128/709–712

[56] References Cited

U.S. PATENT DOCUMENTS

| | | | |
|---|---|---|---|
| 3,215,136 | 11/1965 | Holter et al. | 128/712 |
| 3,585,988 | 6/1971 | Creigh et al. | 128/709 |
| 3,613,669 | 2/1971 | Corbin et al. | 128/712 |
| 3,995,259 | 11/1976 | Harris et al. | 128/712 |
| 4,006,737 | 2/1977 | Cherry | 128/712 |
| 4,088,138 | 5/1978 | Dioch et al. | 128/712 |
| 4,094,310 | 6/1978 | McEacher et al. | 128/712 |
| 4,098,267 | 7/1978 | Stein et al. | 128/712 |
| 4,191,962 | 5/1980 | Sramek | 128/712 X |

FOREIGN PATENT DOCUMENTS 2414235  9/1979  France ................................. 128/712

OTHER PUBLICATIONS

Bacharach, S. L. et al, "A Real-Time System for Multi-Image Gated Cardiac Studies," JNM vol. 18, #1, Jan. 1977.

Graystone, P., "A Simple Method for Displaying Multi-Channel Multiplexed Signals from Digital Magnetic Tape," IEEE BME Trans. v. 17, No. 4, Oct. 1970.

Primary Examiner—Robert W. Michell
Assistant Examiner—Francis J. Jaworski
Attorney, Agent, or Firm—Benasutti Associates, Ltd.

[57] ABSTRACT

An apparatus and method for displaying ECG signals in a format which permits simple and rapid detection of abnormalities in the heart beat. This method and apparatus is particularly suitable for reviewing, at an accelerated rate, heart beat information recorded in real time by portable, patient operated recording equipment over an extended period of time. The system not only detects, identifies, flags and tabulates occurrences of abnormalities, it permits display of the actual waveform for inspection and analysis by a reviewing technician or physician.

16 Claims, 12 Drawing Figures

_Fig. 7_

_Fig. 8_

_Fig. 9_

_Fig. 10_

METHOD AND APPARATUS FOR DISPLAYING ELECTROCARDIOGRAM SIGNALS

BACKGROUND OF THE INVENTION

The present invention generally relates to methods and equipment for monitoring ECG waveforms and more particularly to methods and equipment for ambulatory ECG monitoring, display and analysis.

Ambulatory ECG monitoring is a standard medical diagnostic technique whereby patient electrocardiogram data can be monitored over an extended period, for example 24 hours, by tape recording ECG waveforms using a portable unit operated by the patient, which tape recording is subsequently played back and analyzed in a laboratory, physician's office or other convenient facility.

Normally, the data is originally recorded on the tape at a speed of $3\frac{3}{4}$ inches per minute and then replayed during analysis at an accelerated rate of $3\frac{3}{4}$ or $7\frac{1}{2}$ inches per second. Consequently, the ECG data is displayed to the reviewing technician on an oscilloscopic display at a rate of 60 or 120 times real times speed. The goal of the technician is to find and hard copy abnormal segments of cardiac rhythm for subsequent physician review.

In one prior art display technique, which is disclosed in U.S. Pat. No. 3,215,136 issued to Holter, et al, waveforms representing heart beats; commonly referred to as QRS complexes, are superimposed over each other. The reviewing technician is then expected to discriminate abnormal complexes by their lack of superposition. One problem which was initially encountered in this technique was due to the fact that QRS complexes are asynchronous. Consequently, when displaying these repetitive, asynchronous QRS complexes on a self triggering oscilloscope, the trace patterns would vary along the horizontal or x axis so widely that they would not overlap and a reliable superimposition comparison was difficult, if not impossible.

As disclosed in U.S. Pat. No. 3,229,687 issued to Holter, et al, an attempt to solve this problem of lack of superimposition entailed the use of two pick-up heads which are spaced apart, thereby causing the signal picked up by the second head to be delayed by a predetermined amount of time. The first pick-up head would send a signal to the oscilloscope causing the sweep to start upon the detection of the R wave. The delayed signal from the second head would then be applied to the input of the oscilloscope thereby causing the entire complex to be displayed. Although the subsequent technique improved the degree of superimposition, this technique of displaying abnormalities has some fundamental problems associated therewith. For example, the superimposition technique presents the abnormality to the receiving technician for only a fraction of a second, devoid of its rhythm context. Therefore, a detailed examination of a given ECG sequence requires the stopping of the rapid scan and printing out of the ECG rhythm in real time. In addition, requirements on the operator of total concentration on a superimposed display of 100 to 200 complexes per second as well as the pressure which exists to complete the scan of a 24 hour recording in a reasonable amount of time while constantly stopping the scan to examine and verify questionable segments, can lead to operator fatigue and inaccuracies in data identification.

Some superimposition scanners rely heavily upon analog and digital computer arrhythmia detectors to electronically count and categorize abnormal beats. These detectors often miss abnormal beats, commonly referred to as false negatives, or often count electronic noise or movement artifacts, commonly referred to as false positives, thereby yielding erroneous results. These types of systems are so designed that reliable human review of the correctness of the computer counts and categorizations of abnormal beats is difficult to accomplish.

Another technique, as disclosed in U.S. Pat. No. 3,853,119, issued to Peterson, et al, involves the use of a continuous rhythm scanner which presents a predetermined time segment, for example 2 minutes, of digitally sampled ECG data on a large screen monitor in stationary display to the reviewing technician, at a rate controlled by the technician. Although this technique represents an improvement over the superimposition technique, the ECG data presented to the reviewing technician is merely an approximation of the original analog ECG signal and may be of poor quality due to the relatively slow sampling rate employed in the digitization. In order to improve the quality of the displayed ECG signals to the American Heart Association recommended standard of 0.1 to 100 Hz, a digital continuous rhythm scanner, operating at taped playback speeds of 120 times real time speed, would have to sample at a rate of at least 24,000 samples per second. Although these high sampling rates are achievable using equipment which is presently available, this equipment is relatively expensive, making this technique uncompetitive with the less expensive superimposition method.

SUMMARY OF THE INVENTION

The present invention provides an apparatus and method of displaying, for preselected periods of time, stationary, continuous ECG rhythm in original analog waveform. This is accomplished by numerous features incorporated in applicant's invention.

One such feature is the display of a preselected number of lines of the ECG rhythm in original analog waveform. This display involves the use of a storage cathode ray tube which stores the display of the analog waveform on the face thereof for the pre-selected period of time.

Another feature of the present invention entails the automatic feature enhancing of abnormal beats or rhythms. This feature entails the automatic defocusing and intensification of the beam which traces the waveform on the storage cathode ray tube, over that segment of the display where the abnormality occurs; consequently, the abnormality will be highlighted by the appearance of a broader and brighter trace of the waveform at the point of abnormality.

Yet another feature of the present invention entails the use of a character generator to label the type of abnormality at each occurrence thereof. A further feature of the present invention is the provision of a real time display on the face of the storage cathode ray tube which provides information to the reviewing technician with respect to the times at which the waveforms were being recorded in order that they may be correlated back to their real time occurrences, for example, correlated to certain patient activity, such as sleep, physical exertion, etc.

Accordingly, a primary object of the present invention is the provision of a novel apparatus for displaying and storing segments of stationary, continuous ECG rhythm in original, nondigitized, nonrefreshed, analog waveform.

Another object of the present invention is the provision of an apparatus which automatically highlights abnormalities occurring in the ECG waveform.

A further object of the present invention is the provision of an apparatus which automatically labels the type of abnormality detected by automated detector in proximity to the point on the display where the abnormality occurs in rapid human verification.

Another object of the present invention is the provision of an apparatus which automatically detects, identifies, categorizes, summarizes and displays selected ECG parameters and displays the results in graphic (histogram) form.

An additional object of the present invention is the provision of an apparatus which displays the real time adjacent to the displayed waveform.

A further object of the present invention is the provision of a method of displaying stationary, continuous ECG rhythm in original, analog waveform, which method enhances reliable human review of machine detected abnormalities as well as those which may have gone undetected.

An additional object of the present invention is the provision of a method of displaying stationary, continuous ECG rhythm in original, analog waveform at accelerated playback speeds in a format which reduces operator fatigue.

These and other objects of the present invention will become apparent from the following more detailed description.

DETAILED DESCRIPTION OF THE DRAWINGS

Although specific terms of the invention have been selected for illustration in the drawings and the following description is drawn in specific terms for the purpose of describing these forms of the invention, this description is not intended to limit the scope of the invention which is defined in the appended claims.

Figure 1:
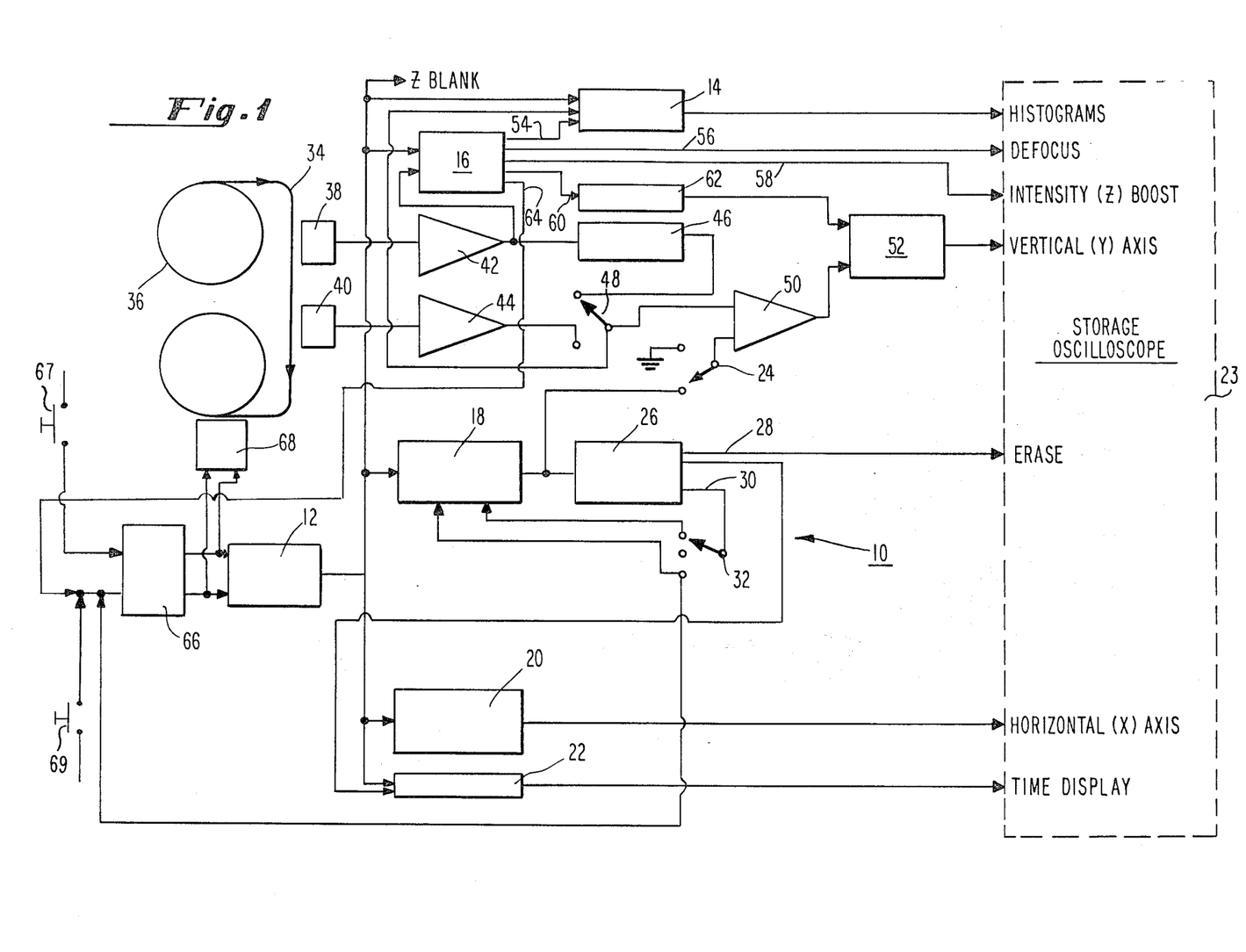
FIG. 1 is a schematic block diagram of a preferred embodiment of the apparatus of the present invention.
Figure 2:
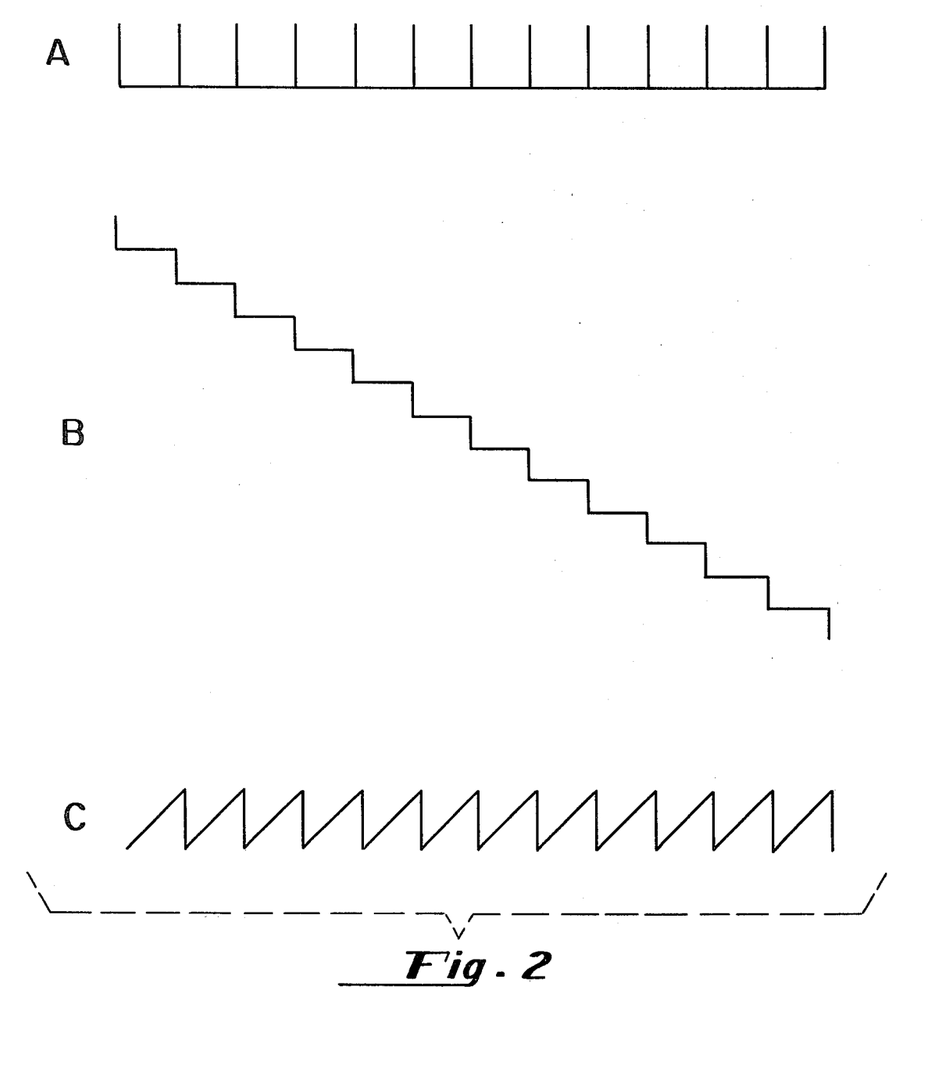
FIG. 2 is a timing diagram showing the relationship of various signals within the apparatus.
Figure 7:
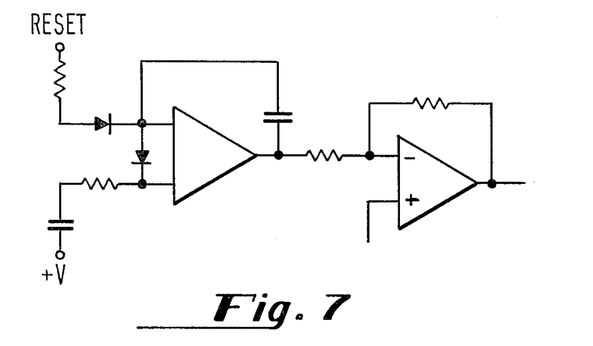
FIG. 7 is a schematic diagram of a descending staircase generator used in the preferred embodiment of the present invention.

Referring to FIG. 1, there is shown a schematic block diagram of the preferred embodiment of the ECG display apparatus of the present invention, generally designated 10. The apparatus 10 includes a clock 12 which generates a timing signal in the form of a series of pulses as shown in FIG. 2A. In the preferred embodiment, the clock 12 is a type 555 timer integrated circuit chip electronically connected in standard clock configuration. The output of the clock 12 is connected to a histogram generator 14, an arrhythmia detector 16, a descending staircase generator 18, a sawtooth generator 20 and a first character generator 22. The descending staircase generator 18, comprises, in the preferred embodiment, a type 3900 operational amplifier in standard up-staircase configuration with an inverting amplifier, for example a type 741, as a second stage, (See FIG. 7). The descending staircase generator 18 outputs a descending staircase signal in synchronization with the timing signal, as shown in FIG. 2B.

Figure 8:
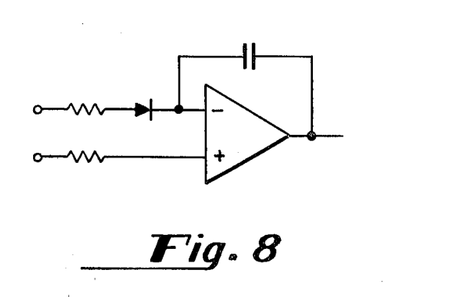
FIG. 8 is a schematic diagram of a sawtooth generator used in the preferred embodiment of the present invention.

The sawtooth generator 20 is, in the preferred embodiment, a type 3900 operational amplifier in standard ramp configuration as shown in FIG. 8. The output of the sawtooth generator is a sawtooth waveform which is produced in sync with the timing signal as shown in FIG. 2C. Consequently as shown in FIG. 2, the output of the descending staircase generator 18 descends one level per clock pulse and the sawtooth generator outputs one sweep sawtooth per clock pulse. The output of the sawtooth generator 20 is electrically connected to the horizontal sweep input of a storage oscilloscope 23. In the preferred embodiment, the storage oscilloscope 23 is a Tektronics, Inc. model 6MA101 19" storage-computer display scope with X, Y, Z boost, erase and defocus beam options, or a Tektronics 613 11" storage scope with the same features.

The output of the descending staircase generator 18 is connected to a first contact, which corresponds to a first position of a first switch 24, as well as to the input to a line counter 26. In the preferred embodiment, the line counter is a type 7490 counter chip. The line counter 26 has a first output 28 and a second output 30. The first output 28 is electrically connected to the erase input of the storage oscilloscope. The line counter 26 generates a signal at the first output 28, at presettable counts, (usually N) which signal causes the stored display on the oscilloscope to be erased. The second output 30 is electrically connected to the rotating contact of a second switch 32. The second output generates a reset signal after counting N staircase transitions, where N is 20 in the preferred embodiment. A first contact, corresponding to a first position of the second switch 32, is electrically connected to a reset input of the descending staircase generator 18.

Figure 9:
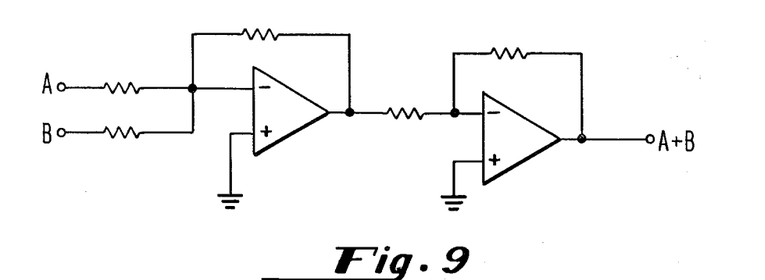
FIG. 9 is a schematic diagram of an adder used in the preferred embodiment of the present invention.
Figure 10:
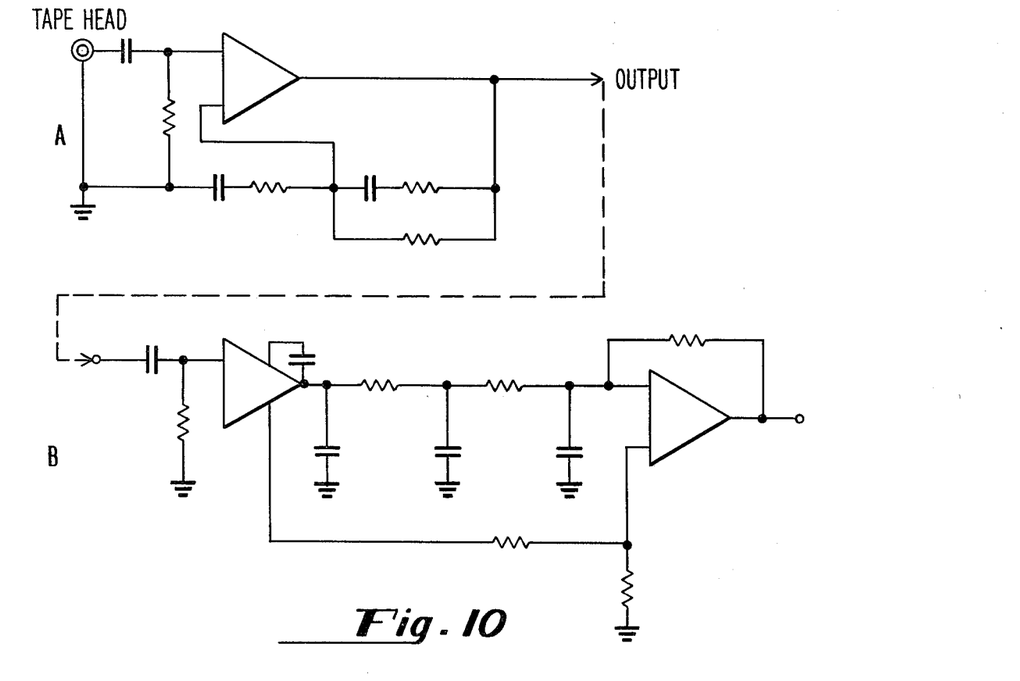
FIG. 10 is a schematic diagram of an amplifier used to amplify the output of a tape deck in the preferred embodiment.

ECG data pre-recorded on a tape 34 at 3¾ inches per minute, then played on a tape deck 36 at accelerated speeds of 7½ or 15 inches per second. In the preferred embodiment, the tape deck 36 is a Teac model AX-3300 two track, with solenoid control and having selectable playback speeds of 7½" and 15" per second. In the preferred embodiment, the tape deck has a first read head 38 and a second read head 40 which are separated by a predetermined distance as will be subsequently described. The output of the first read head 38 is connected to the input of a first amplifier 42 and the output of the second read head 40 is connected to the input of a second amplifier 44. In the preferred embodiment, the first and second amplifiers, 42 and 44, are configured as shown schematically in FIG. 10. Each comprises a National Semiconductor Corp. type LM 1303 Stereo Preamplifier in standard tape head playback preamplifier configuration as shown in circuit A of FIG. 10 and in the "Linear Integrated Circuits" handbook of the National Semiconductor Corp. which handbook is incorporated herein by reference. Note that if the original ECG was recorded via FM modulation, a second stage National LM 565 phase lock loop FM demodulator circuit as shown in circuit B of FIG. 10 is required. The output of the first amplifier 42 is connected to an input of the arrhythmia detector 16 as well as the input of an analog delay 46. In the preferred embodiment, the analog delay 46 is a Radio Shack model number 276-1760 or (276-1761) bucket brigade analog audio delay chip (SAD 1024A). The output of the analog delay 46 is connected to a first contact corresponding to a first position of a third switch 48. The rotating contact of the third switch 48 is electrically connected to one input of an adder 50 as well as to an input of the histogram generator 14. In the preferred embodiment, the adder 50 is a National Semiconductor Corp. type LM 741 operational amplifier electrically connected in standard adder configuration, for example as shown in FIG. 9. The second contact, representing a second position of the third switch 48, is electrically connected to the output of the second amplifier 44.

The output of the adder 50 is electrically connected to one input of a multiplexer 52, for example a National Semiconductor Corp. type AH 5009. A first output 54 of the arrhythmia detector 16 is electrically connected to an input of the histogram generator 14. A second output 56 of the arrhythmia detector 16 is electrically connected to the defocus input of the storage oscilloscope 23. A third output 58 of the arrhythmia detector 16 is electrically connected to the intensity boost control of the storage oscilloscope 23. A fourth output 60 of the arrhythmia detector 16 is electrically connected to the input of a second character generator 62.

Figure 11:
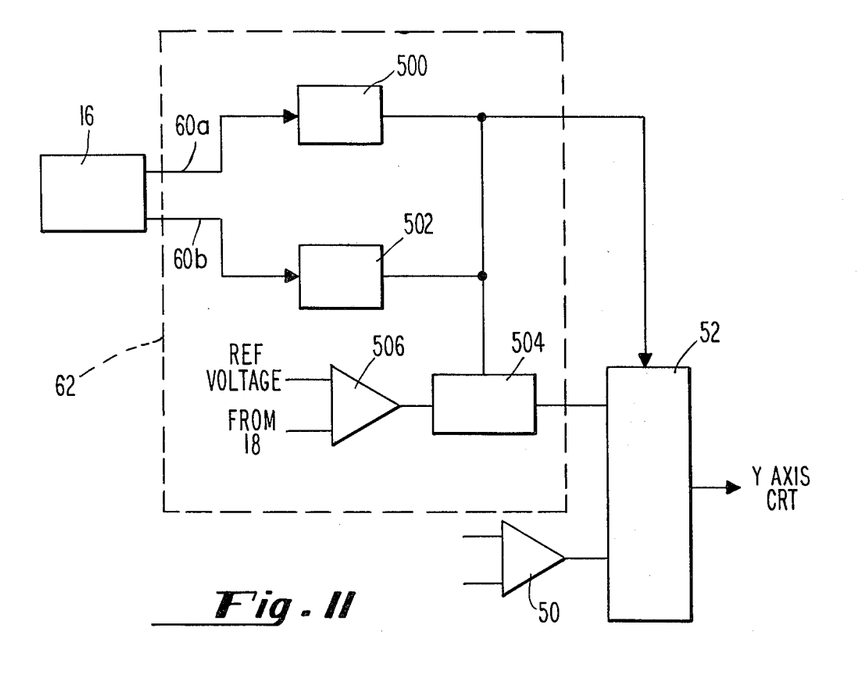
FIG. 11 is a schematic block diagram of a "dot-dash" character generator.

The relationship between the arrhythmia detector 16 and the second character generator 62 is more clearly shown in FIG. 11. In the preferred embodiment, the second character generator 62 is preferrably a "dot-dash" generator, with a dot being defined by a short duration one shot output pulse and a dash being defined by a wider duration one shot pulse. As shown in FIG. 11, the fourth output 60 is, in the preferred embodiment actually two outputs 60a and 60b. Output 60a is connected to the input of a "dot" one shot ,enerator 500 which can be of the type well known in the art. The second output 60b is connected to the input of a "dash" one shot generator 502 which is also of any type well known in the art, the important functional relationship being the output pulse duration of the "dash" one shot 502 be of longer duration than the duration of the output of the "dot" one shot 500. The output of the "dot" one shot 500 and the output of the "dash" one shot 502 are both connected to a control input of a analog switch 504. The output of the descending staircase generator 18 is connected to one input of an adder 506. The other input of the adder 506 is connected to a referenced voltage source which will be subsequently described. The output of the adder 506 is connected to a switched input of the analog switch 504. The switched output of analog switch 504 is connected to an input of the multiplexer 52 as shown in FIG. 1. The outputs of the dot "dot" one shot 500 and the "dash" one shot 502 are connected to a control input of the multiplexer 52 as shown in FIG. 1.

A fifth output 64 of the arrhythmia detector 16 is electrically connected to the stop input of a start stop control 66. In the preferred embodiment, the start stop control 66 is a standard J-K flip flop circuit, for example a National Semiconductor type DM 54H103. The output of the second character generator 62, is electrically connected to a second input of the multiplexer 52. The output of the multiplexer 52 is electrically connected to the vertical (Y) axis input of the storage oscilloscope.

Figure 12:
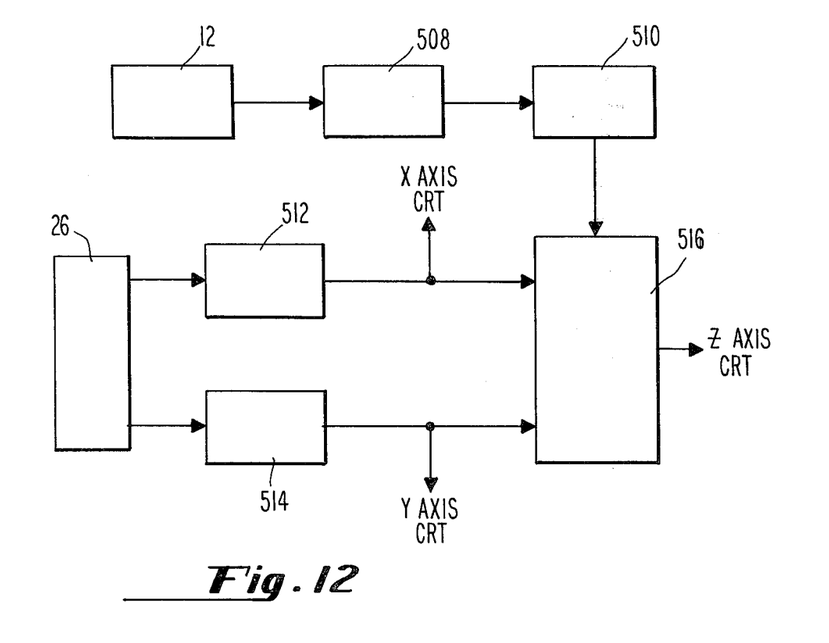
FIG. 12 is a schematic block diagram of a clock display.

The first character generator 22 is configured in accordance with the block diagram shown in FIG. 12. In the preferred embodiment, the first character generator 22 is a clock display generator. The input of the system clock 12 is connected to a counter 508, the output of which is connected to the input of a numeric character generator 510. An output of the line counter 26 is connected to the input of a quadrant sweep generator 512 and a quadrant descending staircase generator 514. The output of the quadrant generator 512 is connected to the X axis input of the oscilloscope 23 and to one input of a video clock display 516. The video clock display 516 is of a type well known in the art, for example a National Semiconductor Corp. type MM 5840 or 53105 or 53100. The output of the quadrant descending staircase generator 514 is connected to the Y axis input of the oscilloscope 23 as well as to an input terminal of the video clock display 516. The output of the video clock display 516 is electrically connected to the Z axis input of the oscilloscope 23.

A third contact, corresponding to a third position of the second switch 32, is electrically connected to the stop input of the start stop control 66. This third contact is also electrically connected to a reset input of the descending staircase generator 18. The start output of the start stop control 66, is electrically connected to a motor control 68 as well as to a start input of the clock 12. The stop output of the start stop control 66 is electrically connected to the motor control 68 as well as to a stop input of the clock 12. The start input of the start stop control 66 is also connected to a manual start control, for example a push button switch, 67. The stop input of the start stop control is also connected to a manual stop control, for example a push button switch 69.

Figure 3:
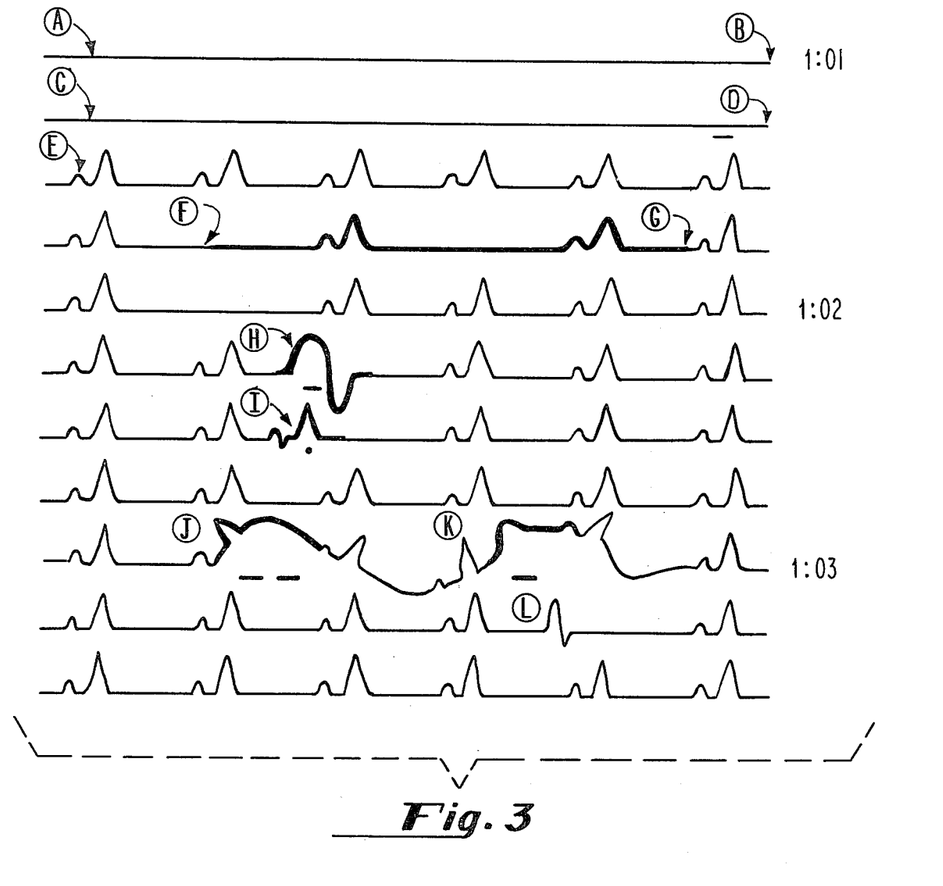
FIG. 3 is a pictorial representation of a typical trace presented by the apparatus of the present invention.

The apparatus 10, operates as follows. As previously stated, the timing signal output of the system clock 12, is a series of brief pulses, as shown in FIG. 2A, that simultaneously cause the descending staircase generator 18 to descend one level per clock pulse, as shown in FIG. 2B, and causes one sweep sawtooth from the sawtooth generator 20 per clock pulse, as shown in FIG. 2C. When the first switch 24 is in the first position, a series of traces will be drawn on the surface of the storage oscilloscope 23 beginning in the upper left hand corner at A as shown in FIG. 3 sweeping to the upper right hand corner (position B in FIG. 3), dropping down one line with blanking on return to the left hand side (position C in FIG. 3), sweeping to the right hand side (position D in FIG. 3), and continuing in this fashion. Note, in the preferred embodiment, blanking is obtained by applying the output of the system clock 12 to null the intensity boost (Z axis). This particular display format occurs because, as previously stated, the output of the sawtooth generator 20 is electrically connected to the horizontal sweep input of the storage oscilloscope 23, and the output of the descending staircase generator 18 is electrically connected to the Y axis input of the storage oscilloscope 23 through the adder 50 in the chopper 52.

The staircase transitions are counted by the line counter 26. After N transitions, the line counter generates a reset pulse which is sent to the descending staircase generator by way of the second switch 32. Upon receipt of the reset pulse, the staircase generator output is reset to its most positive value. Consequently, with the second switch 32 in the first position, the staircase generator 18 will be reset to its high value whenever the line counter 26 counts to N. In addition, when the count reaches N, the line counter 26 internally resets itself to zero and begins to count again.

The ECG data recorded on the tape 34 is sent to the first demodulator amplifier 42 by way of the first read head 38. The output of the first amplifier 42 is the ECG data in analog waveform which is then sent to the electronic arrhythmia detector 16 which, in turn, searches for, categorizes and counts abnormal heart beats or rhythms. The analog output from the first amplifier 42 is also sent to the analog delay 46 where it is electronically delayed by a predetermined period of time x. Consequently, the analog signal at the output of the analog delay 46 is identical to the signal at the output of the first amplifier 42, but is delayed by a time x, where x is equal to the decision time required by the arrhythmia detector 16 to detect, categorize and count the abnormal heart beat or rhythm.

In an alternative preferred embodiment, a delayed analog ECG signal is output from the second amplifier 44. This delay is produced by virtue of the fact that the second read head 40 is displaced by a predetermined distance m from the first read head 38. Consequently, the delay is equal to the distance m between the first and second read heads, 38 and 40, divided by the tape play back speed. Either of these delayed analog signals, can be chosen by way of the third switch 48 which in turn applies the chosen signal to the adder 50 which then adds this delayed signal to the output of the descending staircase generator 18 in order to produce an added signal which is then sent to one input of the multiplexer 52.

If an abnormal beat or rhythm is detected by the arrhythmia detector 16, a signal is sent from the fourth output 60 to the second character generator 62. The signal contains information concerning the type of abnormality, for example: abnormal rhythm, premature ventricular beat, premature atrial beat, etc. For example, if a premature atrial contraction (PAC) is detected, the detector 16 delivers an output pulse at 60a which causes the "dot" one shot 500 to fire, therefore producing a narrow one shot pulse. If a premature ventricular contraction (PVC) is detected, detector 16 outputs a pulse at 60b which causes the "dash" one shot 502 to produce the longer duration one shot pulse. The "dash" and "dot" pulses turn on the analog switch 504 thereby causing the signal produced by the adder 506 to be switched over to the multiplexer 52. The "dash" and "dot" one shot pulses also turn on the multiplexer for the duration of the particular pulse width generated.

The descending staircase generator 18, has vertical steps of voltage V. The adder 506 adds a reference voltage of minus $\frac{1}{2}$ V to minus $\frac{1}{3}$ V to the output of the descending staircase signal, thereby producing a composite signal equal to the descending staircase signal minus ($\frac{1}{2}$ to $\frac{1}{3}$) V. When the multiplexer 52 is on, the output from the adder 506 as well as the output from the adder 50 will be delivered to the Y axis of the storage oscilloscope 23. When the multiplexer 52 is off, the output from the adder 50 will be delivered to the Y axis of the storage oscilloscope 23. When the multiplexer 52 is off, the output from the adder 506 will be open circuited; however, the output from the adder 50 will still be delivered to the Y axis of the storage oscilloscope 23. Consequently, this sequence of events will multiplex the signals from the adder 506 and from the adder 50 on the Y axis of the storage oscilloscope when the "dash" or "dot" one shots are on, but will only allow the output from the adder 50 to appear on the Y axis when they are off. The output of the second character generator 62 as well as the output of the adder 50, are multiplexed by the multiplexer 52 in order to produce a multiplexed signal which is then applied to the Y axis input of the oscilloscope. Consequently, the signal input to the Y axis of the storage oscilloscope 23 is the delayed analog ECG signal added to the output of the descending staircase generator multiplexed with the appropriate identifying character when abnormalities are detected. For example, the output of the adder 50 and the adder 506 are multiplexed and presented to the Y axis of the oscilloscope in a manner so that a dot or dash is drawn below the abnormal beat at a distance of minus ($\frac{1}{2}$ V to minus $\frac{1}{3}$ V) below the base line with the duration of the dot or dash equal to the widths of the dot or dash one shot pulses.

The intensity boost and beam defocus controls of the storage oscilloscope 23 are enabled by the third output 58 and second output 56, respectively, of the arrhythmia detector 16, for a variable amount of time in order to intensify and broaden the CRT beam inscribing the displayed signal during the time of inscription of the abnormal beat or rhythm on the storage tube surface. Consequently, an unintensified, fine line analog ECG signal, is displayed on the storage tube surface during normal heart beats as shown for example on line E of FIG. 3. However, an intensified, broad line analog ECG signal is produced during periods of abnormal rhythm or at times when abnormal beats occur. For example, as shown in FIG. 3, between points F and G, the heart rate has dropped below a predetermined critical level which is recognized by the arrhythmia detector 16. Consequently, this portion of the trace is broadened and intensified. Similarly, the premature ventricular beat occurring at H is intensified, broadly inscribed and identified for example by underlining the occurrence with a dash as shown in FIG. 3-H. In addition, the premature atrial beat occurring at I is intensified, and broadly inscribed and identified, for example by underlining the occurrence with a dot as shown in FIG. 3-I.

Note that at positions J and K in FIG. 3, the patient motion artifact is incorrectly labeled as premature ventricular beats. This error is readily apparent to the technician operator who can see the normal rhythm superimposed on the motion artifact. As a result, the technician would then know to subtract two from the total count of premature ventricular beats as counted by the arrhythmia detector 16. The beat as L has been missed by the electronic arrhythmia detector 16. However, it is readily apparent to the operating technician that the beat at L is abnormal or at least different from normal, and that the arrhythmia detector 16 was probably in error. This segment would then be hard copied for physician review of discrepancy. If categorized as an abnormal beat or as any other type of categorized abnormality, the abnormal beat count to which beat L belongs would be manually augmented by one.

The first output 54 of the arrhythmia detector 16 is connected to an input of the histogram generator 14 for tabulation of abnormal beat and rhythm counts at the exact time location that the abnormalities occurred. The histogram generator 14 receives time information from the system clock 12 and counts the total number of heart beats contained in the delayed analog ECG signal which it receives from the rotating contact of the third switch 48 in order to determine heart rate. An additional feature of the present invention is that manual additions and deletion for correcting errors made by the arrhythmia detector, can be manually entered into the histogram generator 14.

Figure 6:
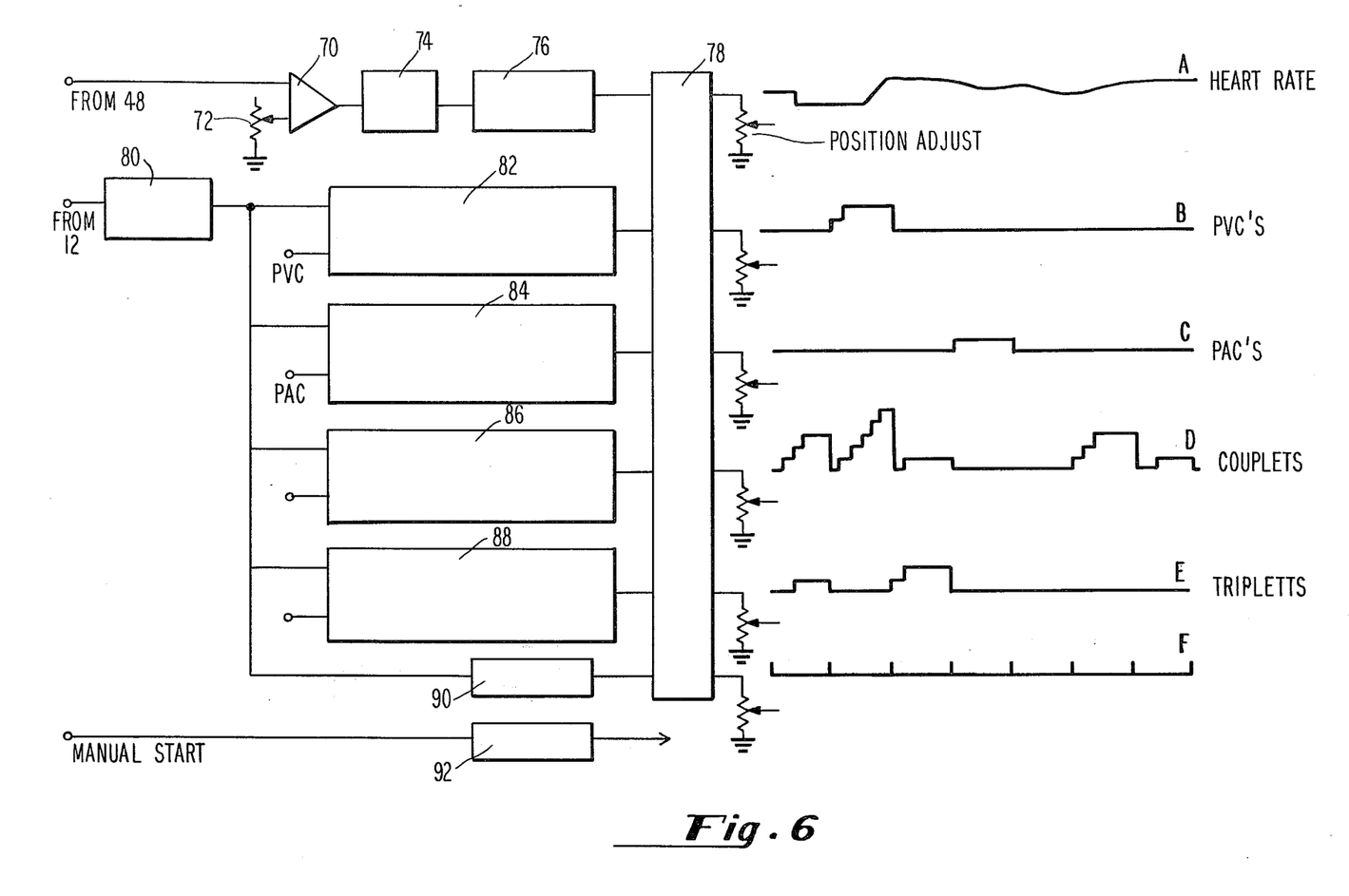
FIG. 6 is a schematic block diagram of a histogram generator of the present invention, showing the typical outputs therefrom.

The histogram generator 14, can be a microprocessor or an analog device; however, the preferred embodiment is that shown in FIG. 6. The analog ECG waveform output from the first amplifier 42 is connected to one input of a comparator 70. The other input of the comparator 70 (National LM 219) is connected to the wiper of potentiometer 72 by which a reference voltage is established. The output of the comparator 70 is conected to the input of a first one shot 74 (National DM 54121). The output of the first one shot 74 is connected the input of a tachometer 76 (National 3900). The output of the tachometer 76 is connected to one input of a chopper 78 (National analog switch AH 5009 in standard multiplexer configuration). The timing signal from the clock 12 is connected to the input of an hour counter 80. The output of the hour counter 80 is connected to the reset input of a first up-staircase generator 82, the reset input of a second up-staircase generator 84, the reset input of a third up-staircase generator 86 and the reset input of a fourth up-staircase generator 88. The output of each up-staircase generator is connected to an input of the chopper 78.

The first output 54 of the arrhythmia detector 16 comprises, in the preferred embodiment, four sub-categorized outputs corresponding to the type abnormalities detected for example: premature ventricular contractions (PVC); premature atrial contractions (PAC); couplets (2 PVC's in a row); and triplets (3 PVC's in a row). The PVC output of the arrhythmia detector 16 is connected to the input terminal of the first up-staircase generator 82. The PVC output of the arrhythmia detector 16 is connected to the input terminal of the second up-staircase generator 84. The couplet output of the arrhythmia detector 16, is connected to the input terminal of the third up-staircase generator 86. The triplet output of the arrhythmia detector 16 is connected to the input terminal of the fourth up-staircase generator 88. The output of the hour counter 80 is connected to the input terminal of a second one shot 90. The output of the second one shot 90 is electrically connected to an input of the chopper 78. The manual start control, for example a push button switch (not shown), is connected to the input of a sawtooth generator 92. The output of the sawtooth generator 92 is connected to the horizontal sweep input of the storage oscilloscope (not shown). The output of the chopper 78 is connected to the vertical input of the storage oscilloscope (not shown). In the preferred embodiment, each up-staircase generator, 82, 84, 86 and 88, is, in the preferred embodiment, a type 3900. The sawtooth generator in the preferred embodiment is a type 3900 in sawtooth configuration.

The histogram generator 14 operates as follows. The analog signal from the rotating contact of the third switch 48 is presented to one input of the comparator 70 which defects every QRS complex in the waveform at a level which is set by the potentiometer 72 in order to produce one output pulse from the first one shot 74 for each QRS in the analog signal. The output of the first one shot 74 is presented to the tachometer 76 whose output is a direct current level which is proportional to the frequency of the first one shot inputs. As previously stated, the first output 54 from the arrhythmia detector 16 comprises, in the preferred embodiment, four outputs from the sub-categorized abnormal beat detectors in the arrhythmia detector 16. For example, every time a PVC is counted by the arrhythmia detector 16, a pulse is generated which augments the output of the first up-staircase generator 82 by one level. Similarly, a PAC output augments the output of the second up-staircase generator by one level, a couplet output augments the output of the third up-staircase generator 86 by one level and a triplet output augments the output of the fourth up-staircase generator 67 by one level. The system clock signal is applied to the input of the hour counter 80, the output of which resets the first, second, third and fourth up-staircase generators to zero every counted hour. In addition, the hour counter 80 triggers the one shot 90 which in turn produces time lines which represent each hour. The outputs of the tachometer 76, first through fourth up-staircase generators 82 through 88 and the second one shot 90 are multiplexed by the chopper 78 and presented to the vertical input of the storage oscilloscope 23. The output of the sawtooth 92, is a single sawtooth which linearly increases from its minimum value to its maximum value over a time period represented by twenty-four pulses from the hour counter 80. This single sweep is initiated by a start command from the manual control switch (not shown). A typical histogram generated trace is shown in FIG. 6. "A" is the heart rate plotted versus time; "B" is the PVC count versus time; "C" is the PAC count versus time; "D" represents the count of couplets versus time; "E" represents the count of triplets versus time; and "F" are time lines, each time preferably equal to one hour of elapsed tape time. This display can be hard copied for subsequent physician review. The vertical calibration for each channel of data is pre-printed on the hard copy paper or drawn by applying a sweep to the vertical Y axis with a calibrater pulse one shot multivibrater applied to the X axis at the beginning and/or end of the sweep created by sawtooth 92. Vertical numbers and letter labels can be drawn by activating a Tektronics type 5403 A3 Readout Circuit at the beginning or end of sweep sawtooth 92.

The system clock signal from the clock 12 is input to the first character generator 22. The first character generator 22 counts and translates into appropriate characters for display of the elapsed tape time on the cathode ray tube surface. The mode of operation of the first character generator 22 is as follows. After one page of ECG data is drawn, the line counter 26, at count N, will enable the quadrant sweep generator 512 and the descending staircase generator 514 to generator one cycle of standard video X-Y coordinates in a particular location on the face of the oscilloscope, for example in the lower right hand corner. The same time, the video clock display 516 modulates the Z axis (beam intensity or video) in order to display the proper numeric character which has been input to it by the numeric character generator 510. The first character generator 22 can be manually advanced to initialize the elapse time clock display to coincide with the actual time that the patient tape was first begun for easy correlation of the patient's symptoms, as recorded in a patient log for example, with detected arrhythmias. Note that the first character generator may alternatively comprise a type 5403 A3 Readout circuit Board assembly Tektronic part #670-2413-00, #155-0015-01 and type 5403 A1 interface board.

The start stop control 66 synchronizes the tape drive motor 68 with the system clock 12. When the manual start control is energized, the start stop control 66 will enable the system clock 12 and simultaneously turn on the tape drive motor 68 by means of the solenoid control in the tape deck. With the second switch 32 in the first position, sequential pages of N lines of continuous ECG data will be displayed and erased with continuous operation of the apparatus until a manual stop command is presented to the start stop control 66. With the second switch 32 in the third position, the line counter 26 will automatically stop the apparatus by applying a signal to the start stop control 66 when the count has reached N. Consequently, one page of N lines of data is displayed and retained on the cathode ray tube screen indefinitely until the next manual start command is applied to the start stop control 66. As an optional feature, the arrhythmia detector 16 can also stop the device by way of a signal appearing at the fifth output 64 which is then applied to the stop input of the start stop device 66. This input appears when an arrhythmia occurs that the arrhythmia detector 20 was programmed to recognize as a stop interrupt. If this optional feature is not selected, and the arrhythmia detector 20 is not programmed to generate a stop interrupt upon the occurrence of an arrhythmia, the ECG data will continue to be displayed until stopped by one of the other modes previously described.

Figure 4:
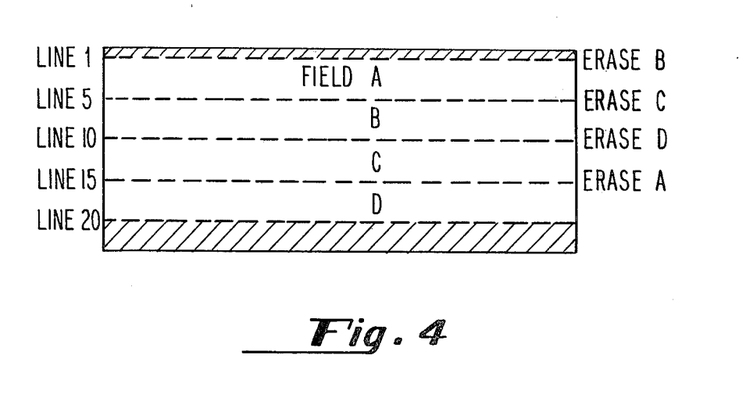
FIG. 4 is a schematic representation of a preferred embodiment of the display divided into four vertical fields.

In storage oscilloscopes with slower erase cycles, it is preferred that the screen be horizontally divided into X fields, where X is greater than or equal to 2, in order that the upper and lower portions of the tube display can be erased sequentially. This feature will allow sufficient phosphor recovery time to accept the next page of ECG data without loss of information while allowing the technician extra time to view the lower fields in the continuous run mode, in which the second switch 32 is in the first position. FIG. 4 is a schematic representation of a preferred embodiment of the display where X equals 4. The four fields are labeled "A", "B", "C", and "D". In this embodiment, a page comprising twenty lines is drawn in 2.5 seconds (this is equivalent to a five minute page at 120 times real time speed). Assuming the typical tube erase cycle requires 0.5 seconds, when the line counter is at line 1, the ECG is being inscribed on line 1 and segment B is given an erase pulse from the line counter 26. By the time the fifth line is inscribed (0.625 seconds after line 1), the "B" field has recovered from the erase cycle which takes 0.5 seconds and is ready to accept the new ECG data. At line 5, the "C" field is erased; at line 10, the "D" field is erased; and at line 15, the "A" field is erased. At line 20, the line counter is reset to one and the cycle repeats until a stop command is entered. This feature permits every field to be viewed by the technician for 2.5 seconds. When a stop command is registered, the ECG data on the storage tube surface can be viewed for a prolonged amount of time or hard copied onto paper by a standard hard copy unit, for example a Tektronics model 4631.

There are two display formats which are favored in the preferred embodiment. The first format uses the storage oscilloscope 23 as the primary display means but in addition includes the option to hard copy one or more pages of oscilloscope display. In this format, a page of N lines of continuous of rhythm analog ECG data is displayed in a format so that the technican can review the entire page of X minutes of data at a glance, without excessive time consuming and fatiguing eye movements. In order to maximize speed and minimize eye fatigue, the following criteria is preferred. For a storage tube having an 11 inch diagonal display surface, N preferably equals 20±6 and X preferably equals 5 or 10 minutes. For a storage tube having a 19 inch diagonal display surface, N preferably equals 25±6 and X preferably equals 5, 10 or 15 minutes. For storage tubes having 5 inch and 7 inch diagonal display surfaces, N preferably equals 10±6 and X preferably equals 4±2. Table 1 lists the preferred sweep periods (i.e. the time required to print one line of data) at various playback speeds (60, 120, and 240 times real time speed) in those cases where 5 and 10 minutes of data are displayed per 20 line page (on 11 inch and 19 diagonal scopes), or where 15 minutes of data are displayed per 30 line page on a 19 diagonal scope. For closeup verification of N=10±6 and X=1.75. This data is tabulated for tapes originally recorded at 3¾ inches per minute, which is the current standard.

It should be noted that the values listed in table 1 are the preferred values for defining the format size, shape, information density and beam writing speed. These values are not intended to limit the scope of the invention to those quantities listed. A factor which was considered in arriving at the preferred values is display flicker. Flicker, which is annoying to the viewer and which can cause eye fatigue, is eliminated where 5 minutes of data is displayed per page at 240 times real speed; corresponding to a sweep period of .0625 second for tapes originally recorded at 3¾ inches per minute and played back at 15 inches per second.

TABLE 1

| Playback Speed | 60 × real time 3¾ ips | 120 × real time 7½ ips | 240 × real time 15 ips |
|---|---|---|---|
| 5 min. page | .25 sec. | .125 sec. | .0625 sec. |
| 10 min. page | .5 sec. | .25 sec. | .125 sec. |
| 15 min. page | .5 sec. | .25 sec. | .125 sec. |

Figure 5:
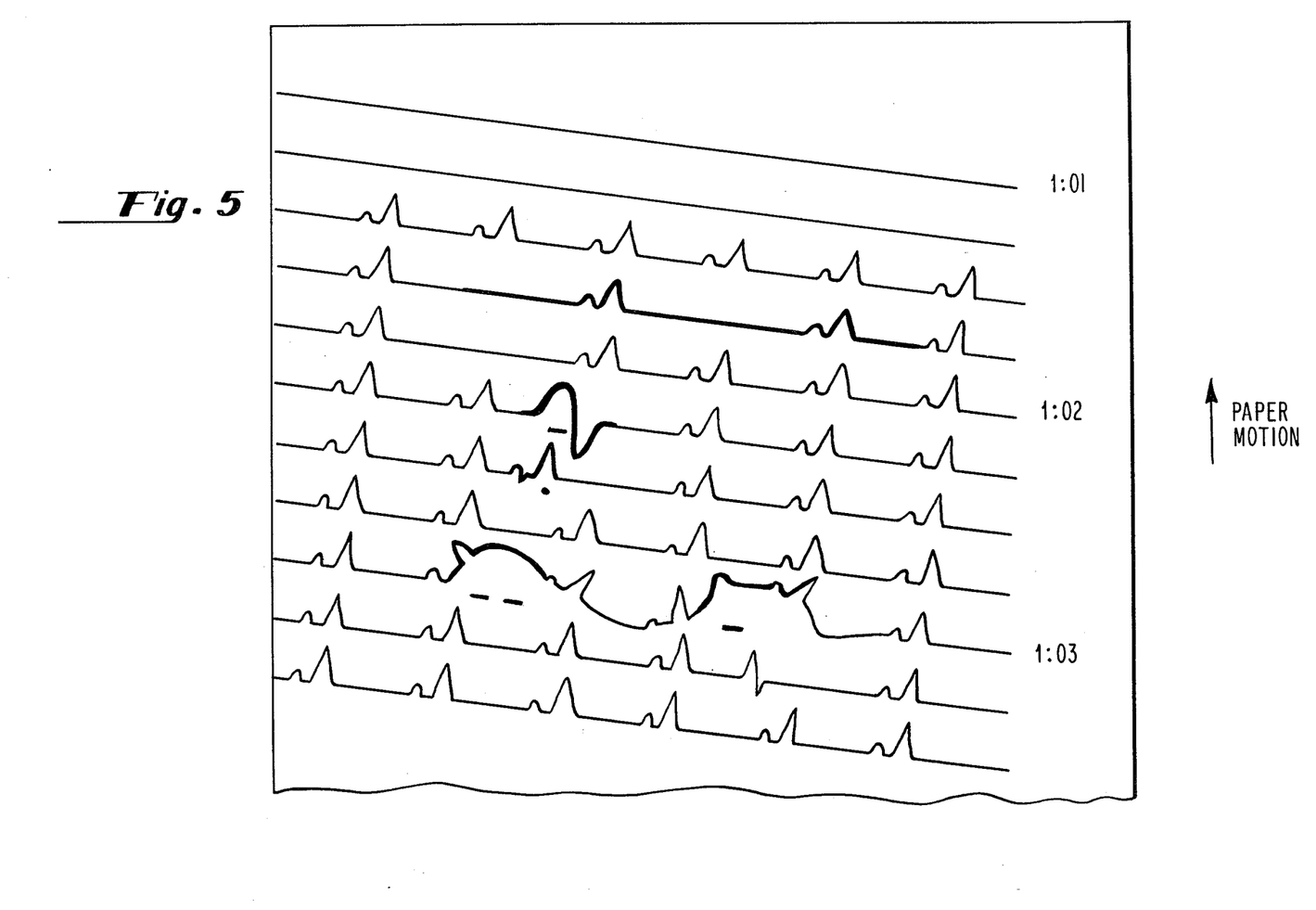
FIG. 5 is a pictorial representation of an alternate preferred embodiment of the display in hard copy form.

A second display format entails hard copying all of the data onto a continuous roll of paper by means of an oscillographic recorder. This can be accomplished, using the apparatus of the present invention as follows. The first switch 24 is placed in the second position which is connected to ground. This causes the input to the multiplexer 52 from the adder 50 to be a replication of the delayed analog ECG signal. The second switch 32 is placed in position 2 which is an unconnected neutral position. The defocus, beam intensity Z boost, vertical (Y) axis, horizontal (X) axis and elapsed time display outputs from the apparatus are disconnected from the storage oscilloscope 23 and reconnected to appropriate input terminals on the oscillographic chart recorder. The descending staircase function required to place N lines on the display surface of the storage cathode ray tube, is replaced by the continuous vertical motion of the paper as shown in FIG. 5, producing a hard copy of the entire tape onto a roll of paper. Note that the continuous lines of ECG data will be slightly sloped if the horizontal sweep is significantly faster than the vertical motion.

As previously stated, the outputs of the descending staircase generator 18 and sawtooth generator 20 were generated by, and in synchronization with, the output of the system clock 12. Note that in the alternative, the output of the descending staircase generator 18 and the output of the sawtooth generator 20 can be triggered by the appearance of a QRS complex thereby ensuring that the display will be synchronous and that none of the QRS complexes will be missed because of abnormal aperiodicity.

As previously stated, the histogram generator 14 can be a microprocessor. In this configuration, the histograms would be generated under the controls of the microprocessor which, would preferably be programmed by instructions which are contained in the same tape containing the ECG data (preferably at the beginning of the tape). In this way, the first information plate back from the patient tape would be instructions to the microprocessor concerning the handling of the data. This would automatically program the microprocessor to handle the subsequent data which is contained on the same tape. This embodiment of the system would significantly enhance versatility.

It will be understood that various changes in the details, materials and arrangements of parts which have been herein described and illustrated in order to explain the nature of this invention may be made by those skilled in the art within the principle and scope of the invention as expressed in the following claims.

What is claimed is:

1. A system displaying physiological signals, such as ECG signals, which signals are reproduced at greater than real time after being recorded in real time for the observation of portions of said signals representing certain cardiac events, said system comprising:
   (a) means for receiving said reproduced ECG signals;
   (b) means for processing, entirely in analog form, said ECG signals for display in a format comprising a plurality of separate vertically displaced lines; and
   (c) a storage oscilloscope for displaying said processed ECG signals in said format.

2. The invention in accordance with claim 1 wherein said apparatus additionally comprises means for generating and displaying time as referenced to the occurrence of said ECG signals.

3. The invention in accordance with claim 1 wherein said system additionally comprises means for making a hard copy of at least a portion of said displayed ECG signals.

4. The invention in accordance with claim 1 wherein said system additionally comprises means for detecting and identifying abnormalities in said ECG signals.

5. The invention in accordance with claim 4, further comprising means for generating a histogram signal for display on said storage oscilloscope, said histogram signal having an amplitude which is representative of the number of occurrences of said abnormalities and which is displayed in a position along the horizontal axis of said storage oscilloscope which position is representative of the time of occurrence of said signal within a predetermined time frame reference.

6. The invention in accordance with claim 4 wherein said means for identifying abnormalities comprises means for intensifying at least a portion of the display of said detected abnormalities.

7. The invention in accordance with claim 4 wherein said means for identifying abnormalities comprises means for displaying a character positioned in proximity to said abnormality.

8. The invention in accordance with claim 7 wherein the configuration of said character is uniquely related to the type of abnormality detected.

9. A method of displaying physiological signals, such as ECG signals, which signals are reproduced at greater than real time after being recorded in real time for the observation of portions of said signals representing certain cardiac events, said method comprising the steps of:
   (a) receiving said reproduced ECG signals;
   (b) processing, entirely in analog form, said ECG signals for display in a format comprising a plurality of separate vertically displaced lines; and
   (c) displaying said processed ECG signals in said format on a storage oscilloscope.

10. The invention in accordance with claim 9 wherein said method additionally comprises the step of generating and displaying time as referenced to the occurrence of said ECG signals.

11. The invention in accordance with claim 9 wherein said method additionally comprises the step of making a hard copy of at least a portion of said displayed ECG signals.

12. The invention in accordance with claim 9 wherein said method additionally comprises the steps of detecting and identifying abnormalities in said ECG signals.

13. The invention in accordance with claim 12 wherein said system additionally comprises the step of generating a histogram signal for display on said storage oscilloscope, said signal having an amplitude which is representative of the number of occurrences of said abnormalities and which is displayed in a position along the horizontal axis of storage oscilloscope, which position is representative of the time of occurrence of said signal within a predetermined time frame reference.

14. The invention in accordance with claim 12 wherein said step of identifying abnormalities comprises intensifying at least a portion of the display of said detected abnormalities.

15. The invention in accordance with claim 12 wherein said step of identifying abnormalities comprises displaying a character positioned in proximity to said abnormalities.

16. The invention in accordance with claim 15 additionally comprising the step of providing a character for each type of abnormality detected wherein the configuration of each character is uniquely related to a particular type of detected abnormality.

* * * * *